United States Patent [19]

Duprez et al.

[11] 4,238,368

[45] Dec. 9, 1980

[54] WATER DEALKYLATION CATALYST OF AROMATIC HYDROCARBONS

[75] Inventors: Daniel Duprez, Poitiers; Michel Grand, Serezin du Rhone, both of France

[73] Assignee: Elf Union, Paris, France

[21] Appl. No.: 970,332

[22] Filed: Dec. 18, 1978

[30] Foreign Application Priority Data

Dec. 19, 1977 [FR] France ............................... 77 38277
Mar. 3, 1978 [FR] France ............................... 78 06159

[51] Int. Cl.$^3$ .......................... B01J 29/04; B01J 29/28
[52] U.S. Cl. .................................. 252/455 Z; 585/483
[58] Field of Search .............. 252/455 Z; 260/672 R; 585/483

[56] References Cited

U.S. PATENT DOCUMENTS

| | | | |
|---|---|---|---|
| 3,354,078 | 11/1967 | Miale et al. ...................... | 260/672 R |
| 3,436,434 | 4/1969 | Lester .............................. | 260/672 R |
| 3,437,709 | 4/1969 | Chloupek ......................... | 260/672 R |
| 3,849,292 | 11/1974 | Gleim ............................... | 252/455 Z |
| 4,139,496 | 2/1979 | Dorawala et al. .............. | 260/672 R |

*Primary Examiner*—Carl F. Dees
*Attorney, Agent, or Firm*—Burgess, Ryan and Wayne

[57] ABSTRACT

Catalyst for water dealkylation of oil fractions containing monoalkylated or polyalkylated aromatic hydrocarbons, said catalyst containing at least one metal of group VIII in a proportion of 0.1 to 5% by weight on a carrier, characterized in that said carrier is a zeolite L that can be exchanged with either alkaline cations or polyvalent cations of groups $V_b$, $VI_b$ and $VII_b$. The zeolite L can be exchanged with a solution of metals such as lithium, sodium, caesium, chromium, manganese, and rhodium. A method of using the catalyst by contacting the hydrocarbons with the catalyst at a temperature of 400°–600° C., a pressure of 0–80 bars, a space velocity of the hydrocarbon of from 0.1 to $10h^{-1}$, and a water to hydrocarbon mol ratio of 2–20.

14 Claims, No Drawings

WATER DEALKYLATION CATALYST OF AROMATIC HYDROCARBONS

BACKGROUND OF THE INVENTION

The object of this invention is a water dealkylation catalyst for monoalkylated or polyalkylated aromatic hydrocarbons that has improved activity, selectivity and stability.

To satisfy the benzene demand, it is possible to dealkylate oil fractions that contain alkylated aromatic hydrocarbons. The treatment with water vapor makes it possible to effect this dealkylation while producing a gas having a high content of hydrogen.

Various processes of water dealkylation have been proposed that make use of catalysts including metals of the group VIII alone or associated with metals of other groups or with metal oxides.

In Haensel U.S. Pat. No. 2,436,923, there is described a catalytic process of demethylation of hydrocarbons, including alkyl aromatic hydrocarbons, by reaction with water or water vapor, in a water/hydrocarbon molar proportion of 2:1 to 12:1, in the presence of a catalyst comprising a metal of group VIII of an atomic number greater than 27 such as cobalt, nickel, ruthenium, rhodium, palladium, osmium, iridium and platinum.

In French Pat. No. 1,588,876, Rabinovich and Maslyanskii have described a dealkylation catalyst containing a noble metal of Group VIII and especially rhodium deposited on an alumina, either pure or doped with nickel or cobalt. A Japanese team of the Mitsubishi Corporation claims in French Pat. No. 2,169,875, the improvement of a rhodium catalyst on alumina by doping the carrier with cerium or uranium. U.S. Pat. Nos. 3,436,433 and 3,646,706 describe a catalyst that contains rhodium deposited on a chromealumina oxide doped with iron and potassium. In German Pat. No. 2,357,407 Girdler describes a water dealkylation process where the carrier of the catalyst, generally alumina, is advantageously exchanged with chromium oxide. In U.S. Pat. No. 4,013,734, Exxon has recently claimed rhodium on alumina dealkylation catalysts improved by doping the carrier with vanadium.

It is observed that in addition to the important part played by the metals of group VIII alone or associated with other metals or metal oxides, the catalyst carrier has an important function in the dealkylation reaction. The carrier must possess at the same time, activity which affects the rate of conversion, selectivity which affects the degradation of the products, and stability which provides extended operation without regeneration.

BRIEF DESCRIPTION OF THE INVENTION

The objects of this invention are improved water dealkylation catalysts, for aromatic hydrocarbons, containing a metal of group VIII of the periodic table on a carrier having a base of zeolite L making possible the realization of high activity, good selectivity and excellent stability.

DETAILED DESCRIPTION OF THE INVENTION

The dealkylation is conducted within a temperature range of from 400° C. to 600° C., preferably from 430° C. to 550° C., ordinarily under a pressure of from 0 to 30 bars, and preferably from 1 to 15 bars.

On the other hand, it has been surprisingly found that if an increase in pressure from 6 to 30 bars does not significantly affect the reaction kinetics, a number of advantages can be obtained by conducting the reaction at a pressure exceeding 30 bars. In this embodiment of the invention, the range of pressure found to be advantageous is from 30 to 80 bars, preferably from 30–60 bars.

The hourly space velocity of the hydrocarbons (LHSV) based on the feed is comprised between 0.1 and 10 $h^{-1}$ and preferably between 0.3 and 4 $h^{-1}$.

The molar ratio between water and hydrocarbon ($H_2O$/HC) in the feed is from 2 to 20, preferably from 4 to 10. A pressure increase of 6 to 30 bars results in a modification of the yield of each of the uncondensed gases: reduction of the yield in carbon oxides and hydrogen and increase of the yield in methane.

On the other hand, multiple advantages result from effecting the reaction at elevated pressures exceeding 30 bars:

the hydrogen produced can then be directly used again in other units such as those of hydrodesulfurization, it is easier and cheaper to effect the dealkylation under elevated pressure by compressing the charge liquids (water and hydrocarbon) than to effect it under medium pressure and re-compress the gas produced for subsequent use, the catalysts already very stable at pressures on the order of 5 bars are still stabler at pressures exceeding 30 bars, finally, the recovery of the hydrocarbons under elevated pressure is much easier than under medium pressure.

Beyond 30 bars a simple condenser can be conceived for recovering the benzene. Below 30 bars it is necessary to add to the condenser a more efficient apparatus for the recovery of the benzene in liquid phase (for example a countercurrent washer or another system based on a process of dissolving or adsorption). It goes without saying that the cost of the recovery system is then higher.

The L zeolites are chabazite-type zeolites having the theoretical formula $M_{g/n}$ $(AlO_2)_9$ $(SiO_2)_{27}$ wherein M is a cation having a valence n. A complete description of said zeolites is given in U.S. Pat. No. 3,216,789. They have cylindrical passages of a diameter of from 7 to 8 Å.

According to a preferred embodiment of the invention, there is used a zeolite L exchanged with alkaline metal cations, particularly lithium, sodium, or potassium. It is easy to exchange 30% of the original cations; the other 70% are situated in places that are more difficult to exchange.

According to another embodiment of the invention, it is possible to introduce a slight acidity by exchanging the zeolite for certain polyvalent cations of the Vb, VIb and VIIb groups such as vanadium, chromium, molybdenum, tungsten and manganese.

The catalyst contains one or more active metals selected from group VIII of the periodic table. Iridium or rhodium are preferably used.

The metals are introduced by impregnation or exchange starting from an aqueous or acid solution of the salt of the metal selected. The total concentration of the metals can fluctuate between 0.1 and 5%, preferably between 0.2 and 1.5% by weight of catalyst.

3

After the introduction of the metal or metals, the catalyst is dried and then calcined in the air. It is reduced before the reaction by contact with a stream of hydrogen at a temperature of from about 400° to 500° C.

After reduction, the catalyst is treated by a current of water vapor at a temperature ranging from about 400° to 600° C. for a period of time of from 5 minutes to 15 hours, preferably 15 minutes to 4 hours.

The Examples that follow, applied to the dealkylation of toluene, are given to illustrate and not to limit the invention.

EXAMPLE 1

Preparation of a catalyst at 0.6% by weight of rhodium deposited on an L sieve of potassium form 220 g of carrier are dried at 140° C. in an air current and then cooled in a dessicator. 3.4 g of hydrated rhodium chloride are dissolved in 110 cm$^3$ of 0.1 N acetic acid. The carrier is immersed in this solution and stirred for 5 minutes, then it is allowed to rest for 1 hour in the air. The volume of solution is calculated in a manner such that all the liquid is absorbed by the carrier. Then the catalyst is dried at 140° C. in air for 4 hours. It is then calcined in two stages: for ½ hour while progressively increasing temperature from ambient to 200° C., then for ½ hour at 500° C. The catalyst is then cooled in a dessicator.

10 g of the catalyst thus prepared are placed in a fixed-bed dynamic reactor in order to be tested under the following conditions: temperature of the bed 450° C.; pressure=1 bar; ppH of the toluene (mass of toluene per mass unit of catalyst per hour) equal to 0.8; molar ratio $H_2O$/toluene=7.8; at the end of two hours of operation the molar yield of benzene in relation to toluene which contacted the catalyst is 0.67, it is 0.83 in relation to converted toluene. At the end of 24 hours of operation, the yields are respectively 0.62 and 0.85. This yield can be maintained for 200 hours by increasing the temperature 1° C. per day.

EXAMPLES II-III-IV-V

These examples of dealkylation in the presence of a catalyst including carriers of gamma alumina are given to permit a comparison with the catalysts of this invention.

The catalyst of Examples II, III and V is a 0.6% rhodium catalyst on gamma alumina.

The catalyst of Example IV is a 0.6% rhodium and 16% nickel oxide catalyst on alumina.

Table 1 herebelow gives the conversion and selectivity obtained in the specified conditions.

The selectivity is understood to be the benzene selectivity, that is, the ratio expressed in % of the number of moles of benzene formed to the number of moles of toluene transformed.

TABLE I

|  | Example II | Example III | Example IV | Example V |
|---|---|---|---|---|
| Temperature | 460° C. | 470° C. | 440° C. | 500° C. |
| Pressure | 1 bar | 15 bars | 1 bar | 2 bars |
| VVH* | 0.5 h$^{-1}$ | 1 h$^{-1}$ | 1 h$^{-1}$ | 0.8 h$^{-1}$ |
| H$_2$O/HC (moles) | 4 | 4 | 4 | 7.8 |
| Conversion | 60% | 48% | 48% | 90% |
| Selectivity | 90% | 89% | 90% | 63% |

*VVH - is the volume of liquid toluene per unit of volume of the catalyst per hour.

The performance of these catalysts is maintained for 30 days if the temperature is increased 1° C. a day.

EXAMPLES VI, VIII, VIII, IX, X

The catalyst used in these examples is a 0.6% rhodium catalyst deposited on a sieve L carrier according to the mode of preparation given in Example 1.

This catalyst is then reduced by hydrogen, then treated with water vapor for 15 minutes at the temperature of the test.

Table II herebelow shows the performances of this catalyst in different conditions of operation. The yields of $H_2$, CO, $CO_2$ and $CH_4$ expressed in moles per mole of toluene passed are respectively: 2.6, 0.10, 0.9, 0.5 for Example VI.

TABLE II

|  | EX. VI | EX. VII | EX. VIII | EX. IX | EX. X |
|---|---|---|---|---|---|
| Temperature | 450° C. | 470° C. | 470° C. | 470° C. | 435° C. |
| Pressure | 2 bars | 2 bars | 2 bars | 2 bars | 2 bars |
| VVH of toluene | 0.6 | 0.6 | 0.6 | 1.2 | 0.6 |
| H$_2$O/HC in moles | 7.8 | 7.8 | 4 | 8 | 8 |
| Conversion | 81% | 90% | 83% | 73% | 62% |
| Selectivity after 6 hours | 80% | 76% | 84% | 85% | 90% |

The comparison of the results obtained in Example VII and in Example V show that the selectivity is clearly improved in the L sieve.

EXAMPLE XI

The catalysts used in this example and in the examples that follow are rhodium catalysts deposited on an L sieve exchanged with a cation other than the original potassium cation.

A lithium-exchanged carrier is prepared in the following manner: 25 g of KL sieve are immersed in 250 cm$^3$ of an aqueous solution M/2 of pure lithium chloride for analyses (76 g/l).

The carrier is slowly stirred for 4 h while boiling the lithium salt solution. It is then cooled and thereafter left for 48 hours at room temperature. The carrier is filtered and then dried at 140° C. It is then impregnated with 0.6% by weight of rhodium according to a method identical with the one that served for impregnating the catalyst of Example I. Even if the carrier is not entirely exchanged with lithium, we shall call it LiL. 10 g of the catalyst No. XI thus prepared (0.6% Rh on LiL) are charged in a fixed-bed dynamic reactor. After reduction by hydrogen and water vapor treatment like in Examples VI to X, the catalyst is tested at 470° C. under 2 bars with a VVH of toluene of 0.6 and an H$_2$O/toluene molar ratio of 8.

There is obtained a conversion of 84% with a benzene selectivity of 85% at the end of 6 hours of operation.

EXAMPLES XII-XIII-XIV-XV

Different L sieve carriers are prepared by exchange with sodium (XII), caesium (XIII), chromium (XIV) and manganese (XV) according to the method of Example XI, that is, starting from an aqueous solution M/2 of a soluble salt of the metal.

These carriers are then impregnated with 0.6% by weight rhodium, dried and calcined in the conditions of Example XI.

The results obtained are recorded in Table III.

EXAMPLE XVI

A catalyst of 0.6% by weight rhodium exchanged on an L sieve (catalyst No. XVI) is prepared in the following manner: 30 g of carrier in the KL form are poured in a solution of 0.49 g of hydrated rhodium chloride in 80 cm$^3$ exchanged water. After vigorously stirring for 5 minutes, it is allowed to stand 16 hours at room temperature. The rhodium is then completely exchanged. The carrier is filtered, dried at 140° C. for 2 hours, and then calcined in the same manner as in Example I.

10 g of the catalyst thus prepared are tested in the same conditions as in Example XI. After 6 hours of operation, a conversion of 91% with a selectivity of 75% is obtained.

TABLE III

|  | XI Li L | XII Na L | XIII Cs L | XIV Cr L | XV Mn L | XVI Rh L |
|---|---|---|---|---|---|---|
| Temperature | 470° C. | 470° C. | 470° C. | 470° C. | 470° C. | 470° C. |
| Pressure | 2 bars | 2 bars | 2 bars | 2 bars | 2 bars | 2 bars |
| V.V.H. (toluene) | 0.6 | 0.6 | 0.6 | 0.6 | 0.6 | 0.6 |
| H$_2$O/HC | 8 | 8 | 8 | 8 | 8 | 8 |
| Conversion | 84% | 89% | 82% | 95% | 88% | 91% |
| Selectivity after 6 h operation | 85% | 74% | 86% | 67% | 80% | 75% |

Examples XVII to XXIII show the good performances of bimetallic catalysts that include rhodium deposited on the L sieve.

EXAMPLE XVII

A catalyst of 0.4% Rh and 0.2% Ir exchanged with L sieve (catalyst No. 17) is prepared as follows: 30 g of KL sieve are placed in 40 cm$^3$ of exchanged water. There are then added 40 cm$^3$ of a solution of 0.6 g hydrochloric acid and 0.34 g rhodium chloride in 0.1 N acetic acid. After stirring, it is allowed to stand for 16 hours. The metals are then completely exchanged. After filtering and drying at 140° C., calcination is carried out as in Example I.

The catalyst tested the same as in Example XI gives a conversion of 75% and a selectivity of 87%.

EXAMPLES XVIII–XXIII

Different monometallic or bimetallic catalysts are prepared as in Example XVII starting from an acetic or hydrochloric acid solution of the metal or metals selected in a manner such that the final composition of the completely exchanged catalyst have the desired value. These catalysts are tested as in Example XI (except for the monometallic catalysts other than rhodium where the test temperature is 525° C.). The results are given in Table IV.

TABLE IV

| Catalyst No. | Metallic composition (carrier sieve KL) | Exchange solution | Test temperature °C. | Conversion | Selectivity |
|---|---|---|---|---|---|
| 18 | 0.4% Rh | acetic | 470 | 70% | 85% |
| 11 | 0.6% Rh | acetic | 470 | 91% | 75% |
| 19 | 0.4% Rh 0.2% Pt | hydrochloric | 470 | 69% | 89% |
| 20 | 0.4% Rh 0.2% Pd | hydrochloric | 470 | 65% | 92% |
| 17 | 0.4% Rh 0.2% Ir | acetic | 470 | 75% | 87% |
| 21 | 0.6% Pt | hydrochloric | 525 | 30% | 100% |
| 22 | 0.6% Pd | hydrochloric | 525 | 29% | 100% |
| 23 | 0.6% Ir | acetic | 525 | 52% | 94% |

Example XXIV shows the good stability of the catalysts with a sieve L base.

EXAMPLE XXIV

Catalyst No. VI is tested for 200 h at 450° C. at the conditions of Example VI under 2 bars and then under 6 bars:

The test results are shown in Table V.

TABLE V

| Duration of operation | Pressure: 2 bars | | Pressure: 6 bars | |
|---|---|---|---|---|
|  | Conversion | Selectivity | Conversion | Selectivity |
| 6 h* | 81% | 80% | 81% | 83% |
| 24 h | 72% | 84% | 75% | 84% |
| 50 h | 65% | 85% | 70% | 85% |
| 200 h | 62% | 85% | 67% | 85% |

*abbreviation for hours

At the end of 200 h, if the temperature is increased 7.0° C., there are again obtained the performances of a working time of 24 h; moreover, the decrease observed at 457° C. between 200 and 300 h of work is identical with that observed at 450° C. between 100 and 200 h of work. The stability is better on catalyst No. VI at 70–75% of conversion than on the catalyst described in the prior art at 50% of conversion.

The following Examples illustrate the results of effecting the reaction under pressures greater than 30 bars:

The Example XXV refers to the improvement on the stability without substantial modification of the benzene yield.

The Example XXVI refers to the improved recovery of the heavy effluents (benzene and toluene) in a condensed phase when working under pressure.

EXAMPLE XXV

The 0.6% rhodium catalyst of Example VI deposited on an L sieve carrier according to the mode of preparation given in Example I was tested at 40 bars, 450° C., VVH 0.6 and an H$_2$O/toluene molar ratio of 7.8. The results are shown in Table VI on which are also given by way of comparison the results obtained at 2 and 6 bars, Examples VI and XXIV, on the same catalyst, all the other conditions being the same (temperature, VVH, H$_2$O/toluene ratio).

TABLE VI

| DURATION OF OPERATION | P = 2 bars | | P = 6 bars | | P = 40 bars | |
|---|---|---|---|---|---|---|
|  | Conv. | Sel. | Conv. | Sel. | Conv. | Sel. |
| 6 h | 81% | 80% | 81% | 83% | 76% | 82% |
| 24 h | 72% | 84% | 75% | 84% | 74% | 83% |
| 50 h | 65% | 85% | 70% | 85% | 73% | 83% |
| 200 h | 62% | 85% | 67% | 85% | 72% | 84% |

Under 40 bars, the yield in benzene is practically equal to the one obtained under 6 bars, but the stability of the catalyst is quite better.

EXAMPLE XXVI

In Table VII are shown the proportions of benzene and toluene that pass to the gaseous phase at the exit of the condenser when the conversion is from 70% to 75%, the same as a 50% conversion for a 2 bar pressure.

TABLE VII

|  | Conversion | Selectivity | % benzene gas | % toluene gas |
|---|---|---|---|---|
| 2 bars | 52% | 94% | 16% | 6% |
| 2 bars | 72% | 84% | 24% | 9% |
| 6 bars | 70% | 85% | 5% | 1.1% |
| 40 bars | 72% | 84% | 0.9% | 0.06% |

It can be seen that a process at low—and even medium—pressure requires a very efficient system of exit from the condenser for the recovery of the hydrocarbons. Beyond 30 bars, the exit of hydrocarbons in the gaseous phase becomes less than 1%, which considerably diminishes their subsequent recovery and as a consequence the investment and operation costs of such a recovery system.

What is claimed is:

1. A water dealkylation catalyst for oil fractions containing alkylated aromatic hydrocarbons which comprises a zeolite L carrier exchanged with cations selected from the group consisting of alkali metal cations, cations from group $V_b$, $VI_b$, and $VII_b$ of the periodic table and mixtures thereof, and containing from about 0.1 to 5% by weight of at least one metal from group VIII of the periodic table.

2. A catalyst according to claim 1, wherein the carrier is a zeolite L of the chabazite type of the theoretical formula $$M_{q/n}(AlO_2)_9(SiO_2)_{27}$$

wherein M is a cation of valence n, having cylindrical ducts of a diameter from 7 to 8 Å.

3. A catalyst according to claim 1 or 2 wherein the carrier is exchanged with a solution of alkali metal cations selected from the group consisting of lithium, sodium and caesium.

4. A catalyst according to claim 1 or 2 wherein the carrier is exchanged with an acetic acid or hydrochloric acid solution of cations selected from the group consisting of cations of metal of group $V_b$, $VI_b$ and $VII_b$ and mixtures thereof.

5. A catalyst according to claim 4 wherein the metal cations are selected from the group consisting of vanadium, chromium and manganese.

6. A catalyst according to claim 4, wherein the introduction of the metals in the exchanged or unexchanged carrier is effected by impregnating the zeolite L, previously dried by heating in air, with an acetic or hydrochloric acid solution of the cations, drying in air, calcining by raising the temperature from ambient to 200° C. in from 30 to 200 minutes and then heating for 30 minutes to 500° C., and cooling the catalyst.

7. A catalyst according to claim 1 or 5, wherein said catalyst is reduced in hydrogen at 400° to 500° C., then contacted with water vapor at a temperature of from 400° to 600° C. for 15 minutes to 4 hours.

8. A catalyst according to claim 1 or 6, which comprises 0.1 to 5% rhodium deposited on the zeolite L.

9. A catalyst according to claim 8 wherein 0.1 to 2% rhodium is deposited on the zeolite L.

10. A catalyst according to claim 1, wherein the zeolite L is partially exchanged with rhodium.

11. A catalyst according to claim 1, containing two metals of the group VIII, the relative proportions of said two metals varying from 1/10 to 10/1.

12. A catalyst according to claim 11 wherein said two metals are rhodium and iridium.

13. A catalyst according to claim 1 containing metals of the group $V_b$, $VI_b$, $VII_b$ and mixtures thereof wherein the total concentration of metals is from 0.1 to 5% by weight of the catalyst.

14. A catalyst according to claim 13 wherein the total concentration of metals is from 0.2 to 1.5% by weight of the catalyst.

* * * * *

UNITED STATES PATENT AND TRADEMARK OFFICE
CERTIFICATE OF CORRECTION

PATENT NO. : 4,238,368
DATED : Dec. 9, 1980
INVENTOR(S) : Daniel Duprez, et al

It is certified that error appears in the above—identified patent and that said Letters Patent is hereby corrected as shown below:

Column 2, line 46: "$M_{g/n}$" should be --$M_{9/n}$--.

Column 4, line 4: "VIII, VIII" should be --VII, VIII--.

Column 5, line 51: "have" should be --has--.

Column 7, line 38, in the formula: "$M_{q/n}$" should be --$M_{9/n}$--.

Signed and Sealed this

Twelfth Day of May 1981

[SEAL]

Attest:

RENE D. TEGTMEYER

Attesting Officer

Acting Commissioner of Patents and Trademarks